(12) United States Patent
Morimoto et al.

(10) Patent No.: US 10,383,778 B2
(45) Date of Patent: Aug. 20, 2019

(54) WEARABLE ARTICLE HAVING ARTWORK

(71) Applicant: The Procter & Gamble Company, Cincinnati, OH (US)

(72) Inventors: Koichi Morimoto, Beijing (CN); Ling Tong, Beijing (CN); Chunmin Cheng, Beijing (CN); Hui Liu, Beijing (CN)

(73) Assignee: The Procter & Gamble Company, Cincinnati, OH (US)

( * ) Notice: Subject to any disclaimer, the term of this patent is extended or adjusted under 35 U.S.C. 154(b) by 381 days.

(21) Appl. No.: 14/836,095

(22) Filed: Aug. 26, 2015

(65) Prior Publication Data

US 2016/0058628 A1   Mar. 3, 2016

(30) Foreign Application Priority Data

Aug. 27, 2014   (WO) .................... CN2014/085249
Feb. 14, 2015   (WO) .................... CN2015/072196

(51) Int. Cl.
| | |
|---|---|
| *A61F 13/15* | (2006.01) |
| *A61F 13/20* | (2006.01) |
| *A61F 13/514* | (2006.01) |
| *A61F 13/49* | (2006.01) |
| *A61F 13/496* | (2006.01) |
| *A61F 13/84* | (2006.01) |

(52) U.S. Cl.
CPC ...... *A61F 13/51496* (2013.01); *A61F 13/496* (2013.01); *A61F 13/49012* (2013.01); *A61F 2013/49025* (2013.01); *A61F 2013/8497* (2013.01)

(58) Field of Classification Search
CPC .............. A61F 13/496; A61F 13/51496; A61F 2013/49025; A61F 2013/8497
See application file for complete search history.

(56) References Cited

U.S. PATENT DOCUMENTS

| | | | |
|---|---|---|---|
| 7,901,393 B2 | 3/2011 | Matsuda et al. | |
| 7,959,620 B2 | 6/2011 | Miura et al. | |
| 2008/0195072 A1 | 8/2008 | Warner | |
| 2013/0310795 A1 | 11/2013 | Glahn et al. | |
| 2013/0317471 A1 | 11/2013 | Morimoto et al. | |
| 2014/0088535 A1 | 3/2014 | Xu et al. | |
| 2017/0290710 A1* | 10/2017 | Morimoto | ......... A61F 13/15203 |

OTHER PUBLICATIONS

PCT International Search Report, dated Jun. 1, 2015 (5 pages).

* cited by examiner

*Primary Examiner* — Michele M Kidwell
(74) *Attorney, Agent, or Firm* — Andrew J. Hagerty; Sarah M. DeCristofaro

(57) ABSTRACT

A wearable article comprising: a main body comprising an outer cover layer and a backsheet attached to the skin-facing surface of the outer cover layer; and a ring-like elastic belt comprising a front belt and a back belt; the backsheet comprising a printed main artwork observable from the garment-facing side of the article. The main artwork exists in the vicinity of the proximal edge of the central panel of at least one of the front and back belts, extends from at least one of the front and back central panels into the crotch panel; and comprises a belt area artwork displayed on the central panel and a crotch area artwork displayed on the crotch panel. The relationship of the opacity of the outer cover layer to the opacity of the central panel overlayed on the garment facing side of the backsheet is defined herein.

18 Claims, 4 Drawing Sheets

WEARABLE ARTICLE HAVING ARTWORK

FIELD OF THE INVENTION

The present invention relates to wearable articles having artworks on both the elastic belt and main body.

BACKGROUND OF THE INVENTION

Infants and other incontinent individuals wear absorbent articles such as diapers to receive and contain urine and other body exudates. Pull-on absorbent articles, or pant-type absorbent articles, are those which are donned by inserting the wearer's legs into the leg openings and sliding the article up into position about the lower torso. Pant-type absorbent articles have become popular for use on children who are able to walk and often who are toilet training, as well as for younger children who become more active in movement such that application of taped-type absorbent articles tends to be more difficult. Absorbent articles are provided with printed artwork to make the article attractive to the wearer and/or the caregiver. Particularly for children, attractive artwork on the article may provide a positive developmental effect. Attractive artwork may be those that connote an undergarment look, are in clear color and shape, or showing characters and objects in noticeable size. Further, attractive artwork may connote high quality to either the wearer or caregiver.

Pant-type absorbent articles having a main body to cover the crotch region of the wearer and a separate elastic belt defining the waist opening and leg opening are known in the art, such as described in PCT Publication WO 2006/17718A. Such pant-type absorbent articles may be referred to as belt-type pants. On the other hand, certain pant-type absorbent articles are configured such that the outer cover of the absorbent body completely covers the entirety of the garment-facing surface of the article. Such pant-type absorbent articles may be referred to as uni-body pants. Belt-type pants, compared to uni-body pants, may be advantageous in that they may have better breathability by having less layers of material in certain areas of the articles, and that they may be manufactured economically. On the other hand, due to the structural difference between the main body and elastic belt, belt-type pants may be disadvantageous in providing printed artwork that provides an integral appearance.

Based on the foregoing, there is a need for a wearable article with attractive artwork. There is also a need for providing such a wearable article without compromise to the performance as an absorbent article, such as fit, wearability, comfort during wear, prevention of sagging, and prevention of leakage. There is further a need for providing such a wearable article in an economical manner.

SUMMARY OF THE INVENTION

The present invention is directed to a wearable article continuous in a longitudinal direction and a transverse direction comprising; a main body comprising an outer cover layer at the most garment-facing side and a backsheet attached to the skin-facing surface of the outer cover layer; and a ring-like elastic belt comprising a front belt and a back belt;

the center of the front belt is joined to a front waist panel of the main body, the center of the back belt is joined to a back waist panel of the main body, the front and back belt each having a left side panel and a right side panel where the main body does not overlap, and the transverse edges of the front belt and the back belt are joined by a seam to form a waist opening and two leg openings, the main body having a crotch panel which is not joined to either the front belt or the back belt;

each front belt and back belt having transversely continuous proximal and distal edges, the proximal edge being located closer than the distal edge relative to the longitudinal center of the article, each of the front belt and back belt each comprise an inner sheet and an outer sheet, wherein the backsheet comprises printing for providing;

a main artwork observable from the garment-facing side of the article, the main artwork existing in the vicinity of the proximal edge of the central panel of at least one of the front and back belts, the main artwork extending from at least one of the front and back central panels into the crotch panel;

the main artwork comprising a belt area artwork displayed on the central panel and a crotch area artwork displayed on the crotch panel;

wherein when the opacity of the outer cover layer is L1; opacity of all of the materials in the central panel overlayed on the garment facing side of the backsheet is L3; and L3−L1=Lg; Lg is less than 28%.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings and which like designations are used to designate substantially identical elements, and in which:

DEFINITIONS

Figure 1:
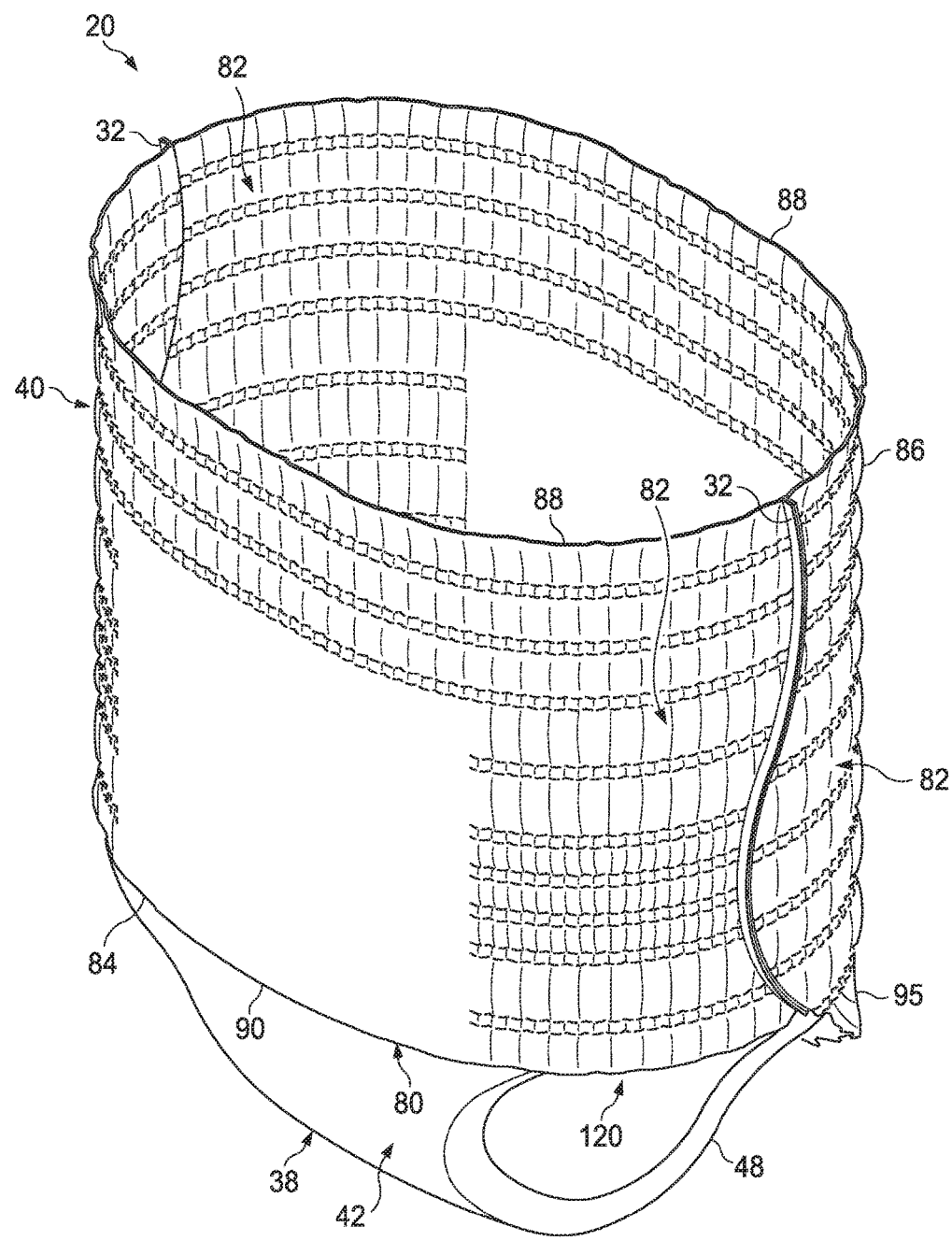
FIG. 1 is a perspective view of one embodiment of a wearable article of the present invention.

As used herein, the following terms shall have the meaning specified thereafter:

"Wearable article" refers to articles of wear which may be in the form of pants, taped diapers, incontinent briefs, feminine hygiene garments, and the like. The "wearable article" may be so configured to also absorb and contain various exudates such as urine, feces, and menses discharged from the body. The "wearable article" may serve as an outer cover adaptable to be joined with a separable disposable absorbent insert for providing absorbent and containment function, such as those disclosed in PCT publication WO 2011/087503A.

"Pant" refers to disposable absorbent articles having a pre-formed waist and leg openings. A pant may be donned by inserting a wearer's legs into the leg openings and sliding the pant into position about the wearer's lower torso. Pants are also commonly referred to as "closed diapers", "prefastened diapers", "pull-on diapers", "training pants" and "diaper-pants".

"Longitudinal" refers to a direction running substantially perpendicular from a waist edge to an opposing waist edge of the article and generally parallel to the maximum linear dimension of the article.

"Transverse" refers to a direction perpendicular to the longitudinal direction.

"Body-facing" and "garment-facing" refer respectively to the relative location of an element or a surface of an element or group of elements. "Body-facing" implies the element or surface is nearer to the wearer during wear than some other element or surface. "Garment-facing" implies the element or surface is more remote from the wearer during wear than some other element or surface (i.e., element or surface is proximate to the wearer's garments that may be worn over the disposable absorbent article).

"Disposed" refers to an element being located in a particular place or position.

"Joined" refers to configurations whereby an element is directly secured to another element by affixing the element directly to the other element and to configurations whereby an element is indirectly secured to another element by affixing the element to intermediate member(s) which in turn are affixed to the other element.

"Film" refers to a sheet-like material wherein the length and width of the material far exceed the thickness of the material. Typically, films have a thickness of about 0.5 mm or less.

"Water-permeable" and "water-impermeable" refer to the penetrability of materials in the context of the intended usage of disposable absorbent articles. Specifically, the term "water-permeable" refers to a layer or a layered structure having pores, openings, and/or interconnected void spaces that permit liquid water, urine, or synthetic urine to pass through its thickness in the absence of a forcing pressure. Conversely, the term "water-impermeable" refers to a layer or a layered structure through the thickness of which liquid water, urine, or synthetic urine cannot pass in the absence of a forcing pressure (aside from natural forces such as gravity). A layer or a layered structure that is water-impermeable according to this definition may be permeable to water vapor, i.e., may be "vapor-permeable".

"Extendibility" and "extensible" mean that the width or length of the component in a relaxed state can be extended or increased.

"Elasticated" and "elasticized" mean that a component comprises at least a portion made of elastic material.

"Elongatable material", "extensible material", or "stretchable material" are used interchangeably and refer to a material that, upon application of a biasing force, can stretch to an elongated length of at least about 110% of its relaxed, original length (i.e. can stretch to 10 percent more than its original length), without rupture or breakage, and upon release of the applied force, shows little recovery, less than about 20% of its elongation without complete rupture or breakage as measured by EDANA method 20.2-89. In the event such an elongatable material recovers at least 40% of its elongation upon release of the applied force, the elongatable material will be considered to be "elastic" or "elastomeric." For example, an elastic material that has an initial length of 100 mm can extend at least to 150 mm, and upon removal of the force retracts to a length of at least 130 mm (i.e., exhibiting a 40% recovery). In the event the material recovers less than 40% of its elongation upon release of the applied force, the elongatable material will be considered to be "substantially non-elastic" or "substantially non-elastomeric". For example, an elongatable material that has an initial length of 100 mm can extend at least to 150 mm, and upon removal of the force retracts to a length of at least 145 mm (i.e., exhibiting a 10% recovery).

DETAILED DESCRIPTION OF THE INVENTION

Figure 2:
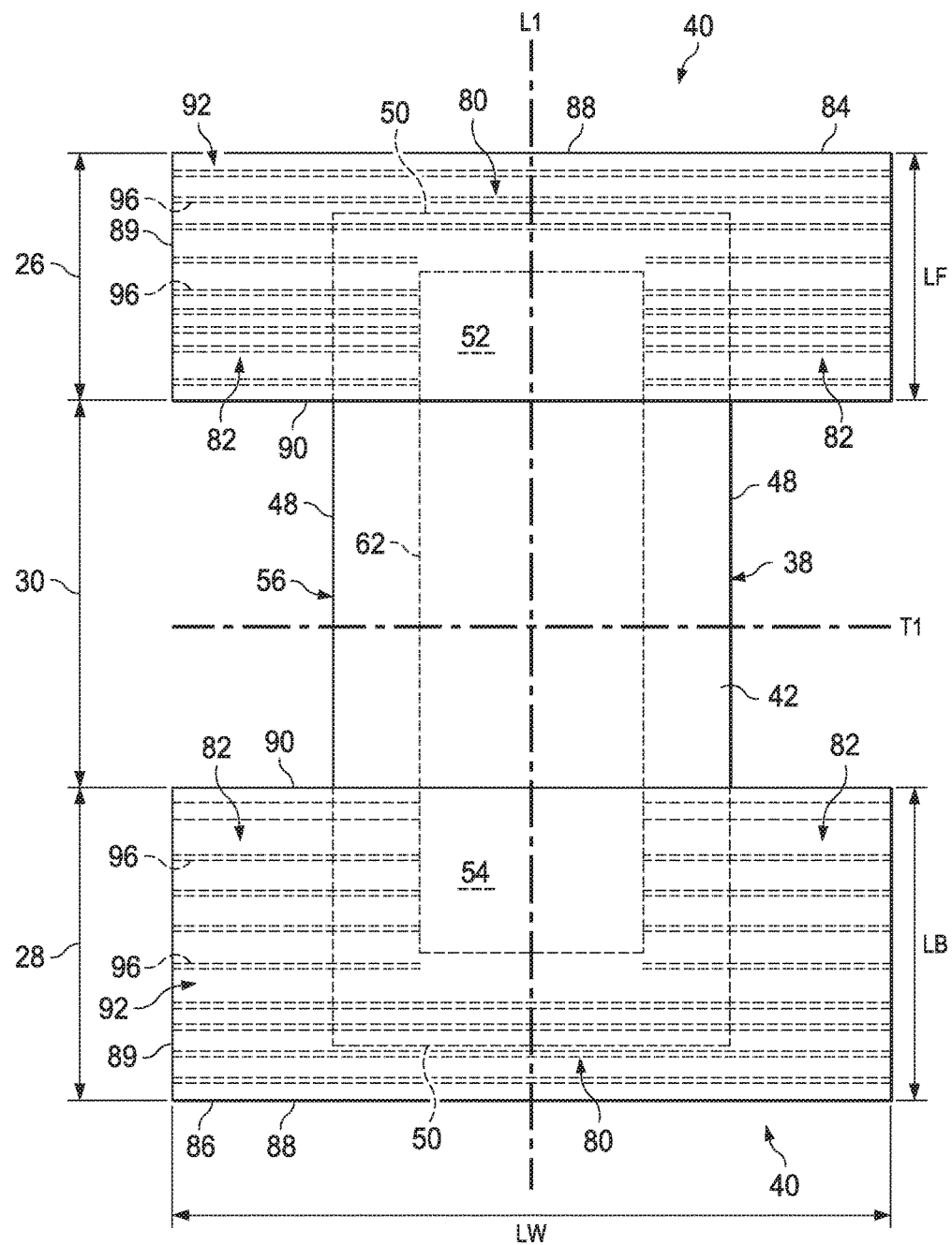
FIG. 2 is a schematic plan view of one embodiment of a wearable article of the present invention with the seams unjoined and in a flat uncontracted condition showing the garment facing surface.

FIG. 1 is a perspective view of an embodiment of the wearable article 20 of the present invention and FIG. 2 is a schematic plan view of the same article with the seams unjoined and in its flat uncontracted condition showing the garment-facing surface. The wearable article 20 has a longitudinal centerline L1 which also serves as the longitudinal axis, and a transverse centerline T1 which also serves as the transverse axis. The wearable article 20 has a skin-facing surface, a garment-facing surface, a front region 26, a back region 28, a crotch region 30, and seams 32 which join the front region 26 and the back region 28 to form two leg openings and a waist opening. The wearable article 20 comprises a main body 38 to cover the crotch region of the wearer, a front belt 84 and a back belt 86 (hereinafter may be referred to as "front and back belts"), the front and back belts 84, 86 forming a ring-like elastic belt 40 (hereinafter may be referred to as "waist belt") extending transversely defining the waist opening. The front and back belts 84, 86 and the main body 38 jointly define the leg openings.

Figure 3:
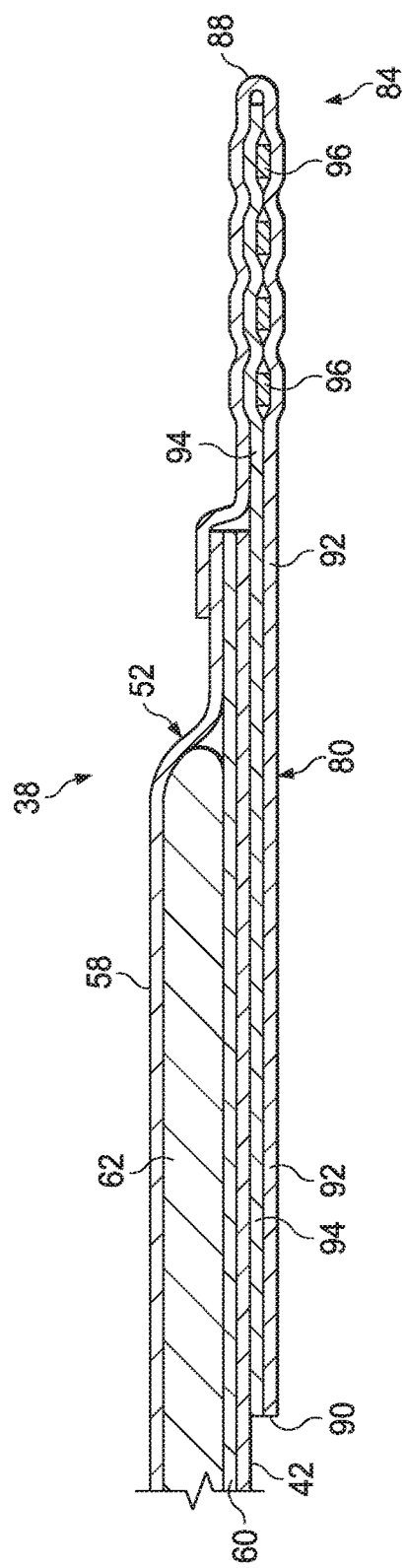
FIG. 3 is a cross section view of FIG. 2 taken along the longitudinal center line in the front region.

Referring now to FIG. 3, the main body 38 comprises a water impermeable backsheet 60 and outer cover layer 42 for covering the garment-facing side of the backsheet 60. The outer cover layer 42 may be a nonwoven sheet. The main body 38 may contain an absorbent core 62 for absorbing and containing body exudates disposed on the main body 38. In the embodiment shown in FIG. 2, the main body 38 has a generally rectangular shape, left and right longitudinally extending side edges 48 (hereinafter may be referred to as "side edge") and front and back transversely extending end edges 50 (hereinafter may be referred to as "end edge"). The main body 38 also has a front waist panel 52 positioned in the front region 26 of the wearable article 20, a back waist panel 54 positioned in the back region 28, and a crotch panel 56 between the front and back waist panels 52, 54 in the crotch region 30. The center of the front belt 84 is joined to a front waist panel 52 of the main body 38, the center of the back belt 86 is joined to a back waist panel 54 of the main body 38, the front and back belts 84, 86 each having a left side panel and a right side panel 82 where the main body 38 does not overlap. The main body has a crotch panel 56 which is not joined to either the front belt 84 or the back belt 86.

Referring to FIGS. 1 and 2, the ring-like belt 40 formed by the front belt 84 and back belt 86 acts to dynamically create fitment forces and to distribute the forces dynamically generated during wear. Herein, the term "proximal" is used to indicate the position of a "proximal" portion being closer relative to the longitudinal center of the article, also closer relative to the crotch panel 56 of the main body 38 than the position of a "distal" portion. Therefore, the proximal edge 90 is located closer than the distal edge 88 relative to the crotch panel 56 of the main body 38. The front and back belts 84, 86 may be joined with each other only at the side edges 89 at the seams 32 to form a wearable article having a waist opening and two leg openings. Each leg opening may be provided with elasticity around the perimeter of the leg opening by the combination of elasticity from the front belt 84, the back belt 86, and any from the main body 38. The front leg opening region 120 is disposed adjacent the leg opening along the proximal edge 90 of the left and right side panels 82 of the front belt 84.

The front and back belts 84, 86 are discontinuous with one another in the crotch region 30. In such embodiment, there is no material that covers the entirety of either the wearer-facing surface or garment-facing surface of the article. The front central panel 80 may partly overlap with the front waist panel 52 of the main body 38. The back central panel 80 may partly overlap with the back waist panel 54 of the main body 38. However, the central panels 80 may not extend into the crotch panel 56 of the main body 38 and not be disposed in the crotch panel 56. In the embodiment shown in FIG. 2, the central panels 80 partly overlap with and is joined to the front waist panel 52 and the back waist panel 54, respectively.

Referring to FIGS. 2 and 3, the front belt 84 and back belt 86 may each comprise an inner sheet 94, an outer sheet 92, (hereinafter also collectively "belt sheets") and configured to impart elasticity to the belt 40. Each of the front and back belts 84, 86 may be made of a single elastic panel, a plurality of elastic panels, or as a laminate having a plurality of belt elastic bodies 96 sandwiched between the inner and outer sheets 94, 92. In one embodiment, the belt elastic bodies 96 extend in the transverse direction to provide a ring like elastic belt 40 when the front belt 84 and the back belt 86 are joined. In one embodiment, at least some of the elastic bodies 96 extend in the transverse direction substantially parallel to each other. In one embodiment, all of the elastic bodies 96 extend in the transverse direction substantially parallel to each other. Such an article may be economically made.

In one embodiment, the transverse width LW of the back belt 86 in the uncontracted condition may be the same as the transverse width of the front belt 84 of the same condition. Such an article may be economically made.

In one embodiment, the longitudinal length LB of the back belt 86 between the back distal edge 88 and the back proximal edge 90 along its entire width LW of the back belt 86 may be approximately the same as the longitudinal length LF of the front belt 84 between the front distal edge 88 and the front proximal edge 90. In such embodiment, the seams 32 close the front and back belt 84, 86 side edges 89 of the same length for forming the article. Such an article may be economically made.

In one embodiment, the back belt 86 may have a greater longitudinal length LB between the back distal edge 88 and the back proximal edge 90 along its entire width LW of the back belt 86 in the transverse direction than the longitudinal length LF of the front belt 84 between the front distal edge 88 and the front proximal edge 90 (FIGS. 1 and 2). In such embodiment, when the wearable article is assembled to form the waist opening and the leg openings, the wearable article 20 is folded along the transverse centerline T1 such that the front distal edge 88 is aligned with the back distal edge 88. The front side edge 89 is also aligned with a portion of the back side edge 89. Then the front belt 84 and the back belt 86 are joined at the front and back side edges 89 at the seams 32. The front and back proximal edges 90, however, may not be aligned to one another. The back proximal edge 90 may be disposed longitudinally closer than the front proximal edge 90 relative to the transverse center line T1 such that the proximal portion of the back side panel 82 extends toward the crotch panel 56 of the main body 38 beyond the front proximal edge 90. The side edge of the proximal portion of the back side panel 82 may not be joined to anywhere and free from attachment. Thus, the proximal portion of the back side panel 82 provides a buttock cover 95 as in FIG. 1.

Referring to FIG. 3, in one embodiment, the outer sheet 92 of the front or back belt towards the distal edge 88 may be longer than the size of the inner sheet 94 in the longitudinal direction, and an end flap of the outer sheet 92 may be folded over the distal end of the inner sheet 94 at the waist opening to form the waist end region. The front and back belts 84, 86 may be provided in low caliper non-woven material for sake of breathability and softness of the belt 40.

Figure 4:
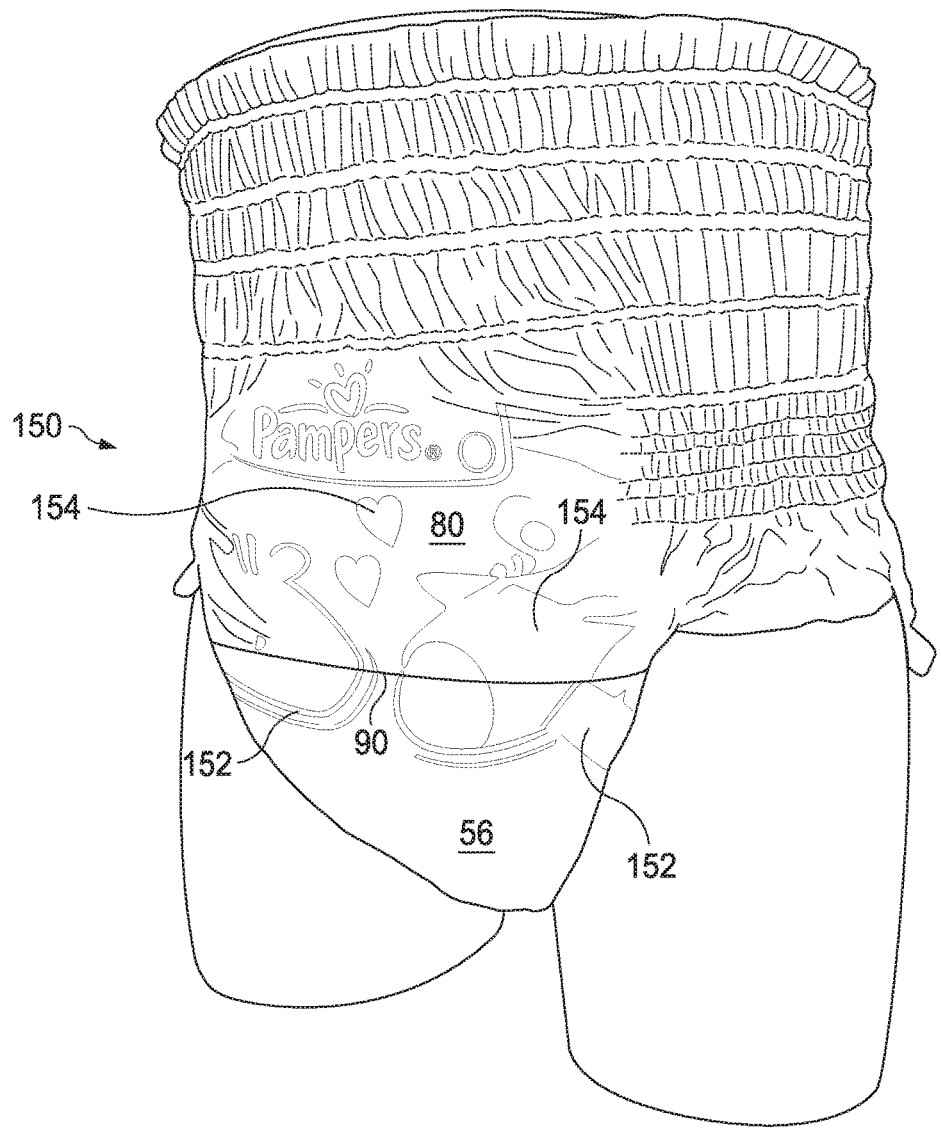
FIG. 4 is a perspective view of one embodiment of a wearable article of the present invention.

Referring to FIGS. 1 and 4, the wearable article 20 of the present invention comprises a main artwork 150 observable from the garment-facing side of the article. The main artwork 150 exists in the vicinity of the proximal edge 90 of the central panel 80 of at least one of the front and back belts 84, 86, the main artwork 150 extending from at least one of the front and back central panels 80 into the crotch panel 56. The main artwork 150 may be displayed on the most easily observed area of the wearable article 20 from at least one of the front or back side of the article when the article is laid flat on a surface, and/or when the article is worn. At least one of the front and back central panels 80 of the front and back belts 84, 86 comprise a belt area artwork 154 observable from the garment-facing side of the article. The crotch panel 56 of the main body 38 comprises a crotch area artwork 152 observable from the garment-facing side of the article. The main artwork 150 may be made of a belt area artwork 154 and a crotch area artwork 152 that are separable graphical elements disposed in the vicinity of each other. In such embodiment, the belt area artwork 154 and the crotch area artwork 152 may have some relationship with each other including, but not limited to, similar objects, similar color, objects changing in time line, etc. The main artwork 150 may be a combined artwork or graphical element comprising a portion of belt area artwork 154 and a portion of crotch area artwork 152 overlapping the proximal edge 90 of the front or back belt. The belt area artwork 154 and crotch area artwork 152 displayed in the vicinity of each other, or overlapping the proximal edge 90, are collectively defined as the main artwork 150. The article may have one or both of a front main artwork 150 and a back main artwork 150. In one embodiment, there may be displayed both front and back main artworks 150 observable from the garment-facing side of the article.

Referring to FIGS. 3 and 4, the artwork as described above are provided as a printing on the garment facing side of the backsheet 60 of the main body 38. The backsheet 60 is made of water impermeable material such as a plastic film. The main artwork 150 is therefore observed through different number of layers of material depending on where the artwork is displayed. The crotch area artwork 152 is observed through at least the outer cover layer 42. The belt area artwork 154 is observed through at least the combination of the outer cover layer 42, and the inner and outer sheets 92, 94 of the belt 40. Due to the difference in number of layers of sheets disposed between the printed surface of the backsheet 60 and the garment facing surface of the article, the crotch area artwork 152 and the belt area artwork 154 may have different visibility in opacity. When the difference in opacity is great, there is a gap in appearance observed between the crotch area artwork 152 and belt area artwork 154, and visual integrity of the main artwork 150 is compromised. The giraffe depicted in FIG. 4 is an example of a main artwork 150 which comprises a crotch area artwork 152 and a belt area artwork 154 which overlaps the proximal edge 90. When a gap in appearance is observed for such a main artwork 150 which overlaps the proximal edge 90, there is a risk that the main artwork 150 may appear as split between the crotch area artwork 152 and belt area artwork 154. Such a split appearance of the main artwork 150 may not be attractive, or may connote low quality.

In the present invention, for preventing the appearance gap as described above and enhancing the visual integrity of the main artwork 150, the opacity of the outer cover layer 42 of the main body, the outer sheet 92 of the belt, and the inner sheet 94 of the belt may be arranged. The opacity of a sheet material is measured according to the "Measurement of Opacity" described below. The article of the present invention has an Lg of less than 28%, or less than 25%, or less than 22%, when Lg is defined as such:

$$L3-L1=Lg$$

L1: opacity of the outer cover layer 42

L2: opacity of the outer sheet 92 and inner sheet 94 combined

L3: opacity of all of the materials in the central panel 80 overlayed on the garment facing side of the backsheet 60

Namely, L3 is the opacity of at least the outer cover layer 42, outer sheet 92 and inner sheet 94 combined, and any other material that may be used in the central panel 80 overlayed on the garment facing side of the backsheet 60. In one embodiment, there is no other material overlayed on the garment facing side of the backsheet 60 other than the outer cover layer 42, outer sheet 92 and inner sheet 94. In such embodiment, L3 is the opacity of the outer cover layer 42, outer sheet 92 and inner sheet 94 combined.

When Lg is higher than 28%, the appearance gap between the crotch area artwork 152 and belt area artwork 154 may be noticeable. The lower the Lg, the less noticeable is the difference in appearance of the crotch area artwork 152 and belt area artwork 154. So long as this relationship is met, any material may be used for the outer cover layer 42, outer sheet 92 and inner sheet 94.

Examples of materials suitable for the outer sheet 92 and inner sheet 94 include nonwoven material of 5-50 g/m$^2$. Nonwoven polyolefins such as polypropylene may be suitable for use. The opacity of the outer sheet 92 and inner sheet 94 combined (L2) may be 20-60%.

Examples of materials suitable for the outer cover layer 42 include nonwoven material of 5-50 g/m$^2$. Patterned, quilted, or embossed material may be useful for connoting softness or high quality of the article. The opacity of the outer cover layer 42 (L1) may be 30-60% or 40-60%.

In one embodiment, the opacity of the outer cover layer 42 (L1) is higher than the opacity of the outer sheet 92 and inner sheet 94 combined (L2). Without being bound by theory, for making L3 as low as possible in order to lower the Lg, one may intuitively desire to make the opacity of the outer sheet 92 and inner sheet 94 combined (L2) as low as possible. The inventors have unexpectedly discovered, however, that counterintuitively, making the opacity of the outer cover layer 42 (L1) higher contributes more in lowering the Lg. Namely, a relatively high opacity of the outer cover layer 42 (L1) mitigates the influence of the opacity of the outer sheet 92 and inner sheet 94 combined (L2), and thus L3 results less deviating from the opacity of the outer cover layer (L1), compared to the configuration wherein an outer cover layer 42 having low opacity is used.

The outer cover layer 42 may be provided opaque by adding a white-tinting/opacifying agent to the polymer resin that is spun to make the nonwoven material. While a variety of whitening/opacifying agents may suffice, it is believed that titanium dioxide (TiO$_2$) may be particularly effective because of its brightness and relatively high refractive index. It is believed that addition of TiO$_2$ to the polymer(s) from which the fibers are to be formed, typically in an amount up to 5.0% by weight of the nonwoven, may be effective to achieve the desired results. It is believed that the increased opacity provided by whitening/opacifying agents helps to produce a visually distinctive, soft appearance of the nonwoven. It also may be desired in some applications that a coloring or tinting agent be added to one or more the polymer resin(s) from which the nonwoven fibers will be spun.

Opacity can also be enhanced by using fiber having cross-sectional shapes other than round and solid (non-hollow) geometries, namely trilobal or multilobal cross-sections, or hollow configurations or combinations thereof. Those non-circular cross-sectional shapes can also provide advantages in terms of loft and compression resilience.

Spunbonding includes the step of calender-bonding a batt of spunlaid fibers, to consolidate them and bond them together to some extent to create the web as a fabric-like structure and enhance mechanical properties e.g., tensile strength, which may be desirable so the material can sufficiently maintain structural integrity and dimensional stability in subsequent manufacturing processes, and in the final product in use. Calender-bonding may be accomplished by passing the batt through the nip between a pair of rotating calender rollers, thereby compressing and consolidating the fibers to form a nonwoven web. One or both of the rollers may be heated, so as to promote heating, plastic deformation, intermeshing and/or thermal bonding/fusion between superimposed fibers compressed at the nip. The rollers may form operable components of a bonding mechanism in which they are urged together by a controllable amount of force, so as to exert the desired compressing force/pressure at the nip. In some processes an ultrasonic energy source may be included in the bonding mechanism so as to transmit ultrasonic vibration to the fibers, again, to generate heat energy within them and enhance bonding.

One or both of the rollers may have their circumferential surfaces machined, etched, engraved or otherwise formed to have thereon a bonding pattern of bonding protrusions and recessed areas, so that bonding pressure exerted on the batt at the nip is concentrated at the bonding surfaces of the bonding protrusions, and is reduced or substantially eliminated at the recessed areas. The bonding surfaces have bonding surface shapes. As a result, an impressed pattern of bonds between fibers forming the web, having bond impressions and bond shapes corresponding to the pattern and bonding surface shapes of the bonding protrusions on the roller, is formed on the nonwoven web. One roller may have a smooth, unpatterned cylindrical surface so as to constitute an anvil roller, and the other roller may be formed with a pattern as described, to constitute a bonding pattern roller; this combination of rollers will impart a pattern on the web reflecting the pattern on the bonding pattern roller. In some examples both rollers may be formed with patterns, and in particular examples, differing patterns that work in combination to impress a combination pattern on the web such as described in, for example, U.S. Pat. No. 5,370,764.

A repeating pattern of bonding protrusions and recessed areas such as S-shapes, diamond shapes, I-shapes, and V-shapes may be formed onto a bonding roller. The bonding shapes of the bonding protrusions impress like-shaped bond impressions on the web in the calendering process. Repeating patterns of S-shapes and I-shapes may be advantageous in providing visual integrity with the gathers of the front and back belts 84, 86.

The bonding protrusions on a roller will have a height, which may be expressed as a difference between the radius of the roller at the outermost (bonding) surfaces of the bonding protrusions, and the radius of the roller at the recessed areas. The height may be adjusted with the objective of minimizing the amount of material that must be removed from the roller surface by machining or etching to create the desired shapes and pattern, while still providing for sufficient clearance between the roller bearing the bonding protrusions and the opposing roller, at the recessed areas, to accommodate passage of the batt through the nip in areas of the batt not to be bonded (i.e., at the recessed areas), without substantially compressing it, because maximum loft/caliper is the objective. For webs of the type and basis weight contemplated herein, a bonding protrusion height between 0.3 mm and 1.0 mm may be desired, or more preferably, a bonding protrusion height between 0.5 mm and 0.8 mm, or even a bonding protrusion height between 0.6 mm and 0.7 mm. The bonding surfaces of the bonding protrusions may have an average area between 0.3 mm$^2$ and 10 mm$^2$. The bonding protrusions typically have sides with an angled slope when viewed in cross section through the height thereof.

Nonwoven webs of the type contemplated herein may be calender-bonded at line speed greater than 300 m/min., or 600 m/min., or even 800 m/min., or more, depending upon nonwoven web composition, basis weight, bonding pattern, and equipment and process variables selected. It will be appreciated that at such speeds, the batt and the surfaces of rollers will entrain surrounding air and move it toward the nip. Surface features of a bonding roller as described above, will enhance this effect. It is believed that, as entrained air is carried toward the nip, the decreasing space between the rollers as the nip is approached creates a zone of relatively higher, and increasing, air pressure in front of the nip. A portion of the entrained air under such higher pressure will be urged into and further compressed in the nip, within the recessed areas of the bonding pattern on the roller, and within the interstices of the fibers passing through the nip. It is believed that, as nonwoven web exits the nip, compressed air entrained within the fibers and passing through the nip therewith encounters a zone of relatively lower pressure on the exit side, and accelerates away from the nip in all unobstructed directions as a result. Thus, it is believed that substantial air entrainment, air compression and complex air flows of relatively high velocity occur within and about the batt and web as a result of movement of the batt and rotation of the calender rollers in the calender-bonding process.

It is believed that surface features of a bonding roller including the bonding protrusions affect these air flows. Particularly at the nip, the profiles of bonding protrusions present obstructions to airflow, while the recessed areas between the bonding protrusions present passageways. Thus, it is believed that for certain configurations, shapes, and positions of bonding protrusions, as will be reflected in the bond impressions created in the web, rotational orientation(s) and repeating patterns of the bonding shapes can be selected and formed to have a beneficial effect on these air flows. It is believed, further, that patterns of bonding protrusions having bonding surface shapes with certain features, reflected in the bonding surfaces and the cross sections of the protrusions along planes substantially parallel with the bonding surfaces, rotational orientations relative the plane approximated by the web surface, and spacing, may be employed to channel these air flows in a way that causes them to reposition the fibers during the calender bonding process, such as by teasing or fluffing the fibers, thus providing an enhanced calender-bonded nonwoven web having greater loft/caliper than a similar nonwoven web having other consolidated bond shapes and patterns, all other variables being the same. Other suitable materials for the outer cover layer 42 of the present invention are disclosed in PCT publication WO 2014/047160, herein incorporated by reference.

As mentioned above, and referring to FIG. 2, the belt 40 formed by the front belt 84 and back belt 86 acts to dynamically create fitment forces and to distribute the forces dynamically generated during wear. Such force may be provided by a plurality of elastic bodies 96 running in the transverse direction. The front and/or back belt 84, 86 may be treated such that certain of the area overlapping the front and/or back waist panel of the main body 38 are removed of elasticity. Removal of elasticity from the area where the belt area artwork 154 is displayed may help the visibility of the belt area artwork 154, and enhance the visual integrity of the main artwork 150. Further, removal of elasticity from certain area of the front and/or back waist panel may be advantageous when the main body 38 comprises an absorbent core 62, in that elasticity in the front and/or back area may cause bunching of the absorbent core 62 and interfere with close fit of the main body 38 to the wearer. In one embodiment, at least a portion of, or at least 10% of, or at least 20% of, or at least 30% of, the elasticity of; at least one of, or at least half of, or at least two thirds of, the elastic bodies are removed in the region overlapping with the front and back waist panels 52, 54 of the main body 38. In one embodiment, the area of all of the elastics 96 overlapping with the belt area artwork 154 may be removed of its elasticity.

The visual integrity of a main artwork 150 overlapping the crotch area artwork 152 and belt area artwork 154 may be further enhanced by providing the color of the belt area artwork 154 with higher color brightness than that of the crotch area artwork 152. The visual integrity may also be enhanced by providing a gradation in color brightness or color intensity to the main artwork 150 in the longitudinal direction.

The main artwork 150 may extend into the vicinity of the longitudinal center of the main body 38. The main artwork 150 may include, or may be arranged with, wetnesss indicators. The main artwork 150 may be coordinated with the shape or color of a disposable tape disposed on the garment-facing side of the outer cover layer 42. The main artwork 150 may extend along the longitudinal side edges of the main body 38. Any of the above mentioned portions of the main artwork 150 may be coordinated with one another for providing an integral appearance of the article. Any of the above mentioned portions of the main artwork 150 may include indicia to describe size, gender, areas suitable for grabbing to wear the article, and other information for use of the article.

The article of the present invention may further be provided with side artwork 160 (not shown) provided on the side panel 82 of the belt 40, or waist artwork 170 (not shown) provided adjacent the distal edge 88 of the belt 40.

Measurement of Opacity

The opacity of a material, or material combined, is the degree to which light is blocked by that material. A higher opacity value indicates a higher degree of light block by the material. Opacity may be measured using a 0° illumination/45° detection, circumferential optical geometry, spectrophotometer with a computer interface such as the HunterLab LabScan XE running Universal Software (available from Hunter Associates Laboratory Inc., Reston, Va.). Instrument calibration and measurements are made using the standard white and black calibration plates provided by the vendor. All testing is performed in a room maintained at about 23±2° C. and about 50±5% relative humidity.

The spectrophotometer is configured for the XYZ color scale, D65 illuminant, 10° standard observer, with UV filter set to nominal. The instrument is standardized according to the manufacturer's procedures using the 44.45 mm (1.750 inch) area view. After calibration, the software is set to the Y opacity procedure which prompts the operator to cover the sample with either the white or black calibration tile during the measurement.

To obtain a specimen, lay the sample flat on a bench, body facing surface downward, and 101.6 mm by 101.6 mm portions of sample are cut using scissor for analysis. When the sample is a combined material, they are overlayed to obtain a specimen. Samples are pre-conditioned at 23° C.±2° C.° and 50%±5% relative humidity for two hours prior to testing.

Place specimen over the measurement port. The specimen should completely cover the port with the surface corresponding to the garment-facing surface of the article directed toward the port. Cover the specimen with the white standard plate. Take a reading, then remove the white tile and replace it with the black standard tile without moving the specimen. Obtain a second reading, and calculate the opacity as follows:

$$\text{Opacity} = (Y \text{value}_{(black\ backing)} / Y \text{value}_{(white\ backing)}) \times 100$$

A total of three identical material, or materials combined, are analyzed and their opacity results recorded. Calculate and report the average opacity to the nearest 0.1%.

Example 1

Samples A-F having the structure of the belt-type wearable article of the present invention of FIGS. 1-3, and having differences in constructions of the outer cover layer 42, outer sheet 92 and inner sheet 94, as in Table 1, were assembled. All samples are provided with the same main artwork 150 as shown in FIG. 4 having a main artwork 150 graphic overlapping the crotch area artwork 152 and belt area artwork 154. The visual integrity of the main artwork 150 was observed by a trained expert panel and evaluated as such; "Bad": the gap at the proximal edge is clearly observed; "Good": the gap at the proximal edge is difficult to observe. The results are shown in Table 1 below.

TABLE 1

| Sample | g/m² of outer cover layer | L1 | g/m² of outer and inner sheet | L2 | L3 | Lg | Visual integrity |
|---|---|---|---|---|---|---|---|
| A | 17 | 20.1% | 17 + 10 | 37.4% | 50.0% | 29.9% | Bad |
| B | 17 | 20.1% | 17 + 17 | 36.4% | 49.2% | 29.1% | Bad |
| C | 17 | 20.1% | 17 + 25 | 51.6% | 61.4% | 41.3% | Bad |
| D | 25 | 45.4% | 17 + 10 | 37.4% | 65.9% | 20.4% | Good |
| E | 25 | 45.4% | 17 + 17 | 36.4% | 65.3% | 19.8% | Good |
| F | 25 | 45.4% | 17 + 25 | 51.6% | 73.6% | 28.2% | Bad |

Inventive Samples D and E of the present invention having an Lg of less than 28% provided improved visual integrity of the main artwork compared to comparative samples A-C and F having an Lg of more than 28%. Inventive Samples D and E further provide perceived softness and quality.

Consumer Acceptance

Comparative Sample B and Inventive Sample E described in Example 1 were subjected to a consumer test of 10 panelists. The panelists were caregivers of Chinese Size 4 (L-size) wearers who regularly use Merries or Huggies brand pant diaper products. The panelists were given both Comparative Sample B and Inventive Sample E and asked to choose which product has a "graphic looking uniformly integrated". The percentage of choices was statistically analyzed. Test results are shown below in Table 2.

TABLE 2

| Comparative Sample B | Inventive Sample E | No preference |
|---|---|---|
| 10% | 80% (*) | 10% |

(*) Statistically significant over others with 90% confidence level

According to the consumer acceptance test results, Inventive Sample E of the present invention, compared to Comparative Sample B, was statistically significantly better accepted in providing visual integrity of the graphic.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A wearable article continuous in a longitudinal direction and a transverse direction comprising: a main body comprising an outer cover nonwoven layer at the most garment-facing side and a backsheet attached to the skin-facing surface of the outer cover layer; and a ring-like elastic belt comprising a front belt and a back belt;

the center of the front belt is joined to a front waist panel of the main body, the center of the back belt is joined to a back waist panel of the main body, the front and back belt each having a left side panel and a right side panel where the main body does not overlap, and the transverse edges of the front belt and the back belt are joined by a seam to form a waist opening and two leg openings, the main body having a crotch panel which is not joined to either the front belt or the back belt;

each front belt and back belt having transversely continuous proximal and distal edges, the proximal edge being located closer than the distal edge relative to the longitudinal center of the article, each of the front belt and back belt each comprise an inner nonwoven sheet and an outer nonwoven sheet, wherein the backsheet comprises printing for providing:

a main artwork observable from the garment-facing side of the article, the main artwork existing in the vicinity of the proximal edge of the central panel of at least one of the front and back belts, the main artwork extending from at least one of the front and back central panels into the crotch panel;

the main artwork comprising a belt area artwork printed on a first surface of the backsheet and displayed on the central panel and a crotch area artwork printed on the first surface of the backsheet and displayed on the crotch panel;

wherein when the opacity of the outer cover layer is $L1$; the total opacity created by the outer cover nonwoven layer, the inner nonwoven sheet, and the outer nonwoven sheet, combined in the central panel overlayed on the garment facing side of the backsheet is $L3$; $L3-L1=Lg$; and $Lg$ is about 28% or less, wherein the opacity of the outer nonwoven sheet and inner nonwoven sheet combined is $L2$, and $L1$ is greater than $L2$, and wherein a number of nonwoven layers between the belt area artwork and an outermost article surface portion overlying the belt area artwork is different than a number of nonwoven layers between the crotch area artwork and an outermost article surface portion overlying the crotch area artwork.

2. The article of claim 1, wherein $Lg$ is less than about 25%.

3. The article of claim 2, wherein $Lg$ is less than about 22%.

4. The article of claim 1, wherein $L1$ is from about 30 to about 60%.

5. The article of claim 4 wherein the outer cover layer is a nonwoven material comprising polymer resin comprising about 5% or less, titanium dioxide.

6. The article of claim 1, wherein the main artwork comprises the belt area artwork and the crotch area artwork that are separable graphical elements.

7. The article claim 1, wherein the main artwork comprising the belt area artwork and the crotch area artwork overlaps the proximal edge.

8. The article of claim 7, wherein the color brightness of the belt area artwork is greater than the color brightness of the crotch area artwork.

9. The article of claim 7, wherein the main artwork is provided in gradation of color brightness or color intensity in the longitudinal direction.

10. The article of claim 1, wherein the inner and outer sheets comprise a plurality of elastic strands sandwiched therebetween and running in the transverse direction, the elasticity of the elastic strands being removed at areas where the belt area artwork is displayed.

11. The article of claim 1, further comprising an absorbent core.

12. The article of claim 1, comprising both of a front main artwork and a back main artwork, each observable from the garment-facing side of the article.

13. The article of claim 1, wherein the materials overlaying the garment facing side of the backsheet consist essentially of the outer cover layer, an outer sheet, and an inner sheet.

14. The article of claim 1, wherein the main artwork comprises a wetness indicator.

15. A wearable article continuous in a longitudinal direction and a transverse direction comprising: a main body comprising an outer cover nonwoven layer at the most garment-facing side and a backsheet attached to the skin-facing surface of the outer cover layer; and a ring-like elastic belt comprising a front belt and a back belt;

the center of the front belt is joined to a front waist panel of the main body, the center of the back belt is joined to a back waist panel of the main body, the front and back belt each having a left side panel and a right side panel where the main body does not overlap, and the transverse edges of the front belt and the back belt are joined by a seam to form a waist opening and two leg openings, the main body having a crotch panel which is not joined to either the front belt or the back belt;

each front belt and back belt having transversely continuous proximal and distal edges, the proximal edge being located closer than the distal edge relative to the longitudinal center of the article, each of the front belt and back belt each comprise an inner nonwoven sheet and an outer nonwoven sheet, wherein the backsheet comprises printing for providing:

a main artwork observable from the garment-facing side of the article, the main artwork existing in the vicinity of the proximal edge of the central panel of at least one of the front and back belts, the main artwork extending from at least one of the front and back central panels into the crotch panel;

the main artwork comprising a belt area artwork printed on a first surface of the backsheet and displayed on the central panel and a crotch area artwork printed on the first surface of the backsheet and displayed on the crotch panel;

wherein when the opacity of the outer cover layer is $L1$; the total opacity created by the outer cover nonwoven layer, the inner nonwoven sheet, and the outer nonwoven sheet, combined in the central panel overlayed on the garment facing side of the backsheet is $L3$; $L3-L1=Lg$; and $Lg$ is about 28% or less, and wherein a number of nonwoven layers between the belt area artwork and an outermost article surface portion overlying the belt area artwork is different than a number of nonwoven layers between the crotch area artwork and an outermost article surface portion overlying the crotch area artwork.

16. The article of claim 15, wherein $Lg$ is less than about 25%.

17. The article of claim 15, wherein $Lg$ is less than about 22%.

18. A wearable article continuous in a longitudinal direction and a transverse direction comprising: a main body comprising an outer cover nonwoven layer at the most garment-facing side and a backsheet attached to the skin-facing surface of the outer cover layer; and a ring-like elastic belt comprising a front belt and a back belt;

the center of the front belt is joined to a front waist panel of the main body, the center of the back belt is joined to a back waist panel of the main body, the front and back belt each having a left side panel and a right side panel where the main body does not overlap, and the transverse edges of the front belt and the back belt are joined by a seam to form a waist opening and two leg openings, the main body having a crotch panel which is not joined to either the front belt or the back belt;

each front belt and back belt having transversely continuous proximal and distal edges, the proximal edge being located closer than the distal edge relative to the longitudinal center of the article, each of the front belt and back belt each comprise an inner nonwoven sheet and an outer nonwoven sheet, wherein the backsheet comprises printing for providing:

a main artwork observable from the garment-facing side of the article, the main artwork existing in the vicinity of the proximal edge of the central panel of at least one of the front and back belts, the main artwork extending from at least one of the front and back central panels into the crotch panel;

the main artwork comprising a belt area artwork printed on a first surface of the backsheet and displayed on the central panel and a crotch area artwork printed on the first surface of the backsheet and displayed on the crotch panel;

wherein when the opacity of the outer cover layer is $L1$; the total opacity created by the outer cover nonwoven layer, the inner nonwoven sheet, and the outer nonwoven sheet, combined in the central panel overlayed on the garment facing side of the backsheet is $L3$; $L3-L1=Lg$; and $Lg$ is about 28% or less.

* * * * *